(12) United States Patent
Yamanaka et al.

(10) Patent No.: US 11,479,803 B2
(45) Date of Patent: Oct. 25, 2022

(54) β-1, 6-GLUCANASE MUTANT, AND METHOD FOR MEASURING β-1, 6-GLUCAN

(71) Applicant: TOEI SHINYAKU CO., LTD., Tokyo (JP)

(72) Inventors: Daisuke Yamanaka, Tokyo (JP); Naohito Ohno, Tokyo (JP); Masuro Motoi, Tokyo (JP); Akitomo Motoi, Tokyo (JP)

(73) Assignee: TOEI SHINYAKU CO., LTD., Tokyo (JP)

( * ) Notice: Subject to any disclaimer, the term of this patent is extended or adjusted under 35 U.S.C. 154(b) by 304 days.

(21) Appl. No.: 16/613,487

(22) PCT Filed: May 11, 2018

(86) PCT No.: PCT/JP2018/018346
§ 371 (c)(1),
(2) Date: Nov. 14, 2019

(87) PCT Pub. No.: WO2018/212095
PCT Pub. Date: Nov. 22, 2018

(65) Prior Publication Data
US 2021/0155970 A1    May 27, 2021

(30) Foreign Application Priority Data
May 16, 2017 (JP) .............................. JP2017-097613

(51) Int. Cl.
*C12Q 1/40* (2006.01)
*C12N 9/24* (2006.01)

(52) U.S. Cl.
CPC ............. *C12Q 1/40* (2013.01); *C12N 9/2402* (2013.01); *C12Y 302/01075* (2013.01)

(58) Field of Classification Search
None
See application file for complete search history.

(56) References Cited

U.S. PATENT DOCUMENTS

| 6,022,723 A * | 2/2000 | Kofod ............ C12Y 302/01075 |
| | | 435/945 |
| 10,463,711 B2 * | 11/2019 | Hamill ....................... A23L 2/66 |
| 2012/0009594 A1 * | 1/2012 | Yoneda ............ C07K 14/43509 |
| | | 435/7.4 |

OTHER PUBLICATIONS

Oyama, Seiji et al. Cloning and Expression of an Endo-1,6-β-D-glucanase Gene from Neurospora crassa. Biosci. Biotechnol. Biochem., 66 (6), pp. 1378-1381. (Year: 2002).*
Livingstone, Craig et al. Protein Sequence Alignments: a Strategy for Hierarchical Analysis of Residue Conservation. Cabios. vol. 9 , No. 6. pp. 745-756. (Year: 1993).*
Temple et al. "A Bacteroidetes locus dedicated to fungal 1,6-β-glucan degradation: Unique substrate conformation drives specificity of the key endo-1,6-β-glucanase", J. Biol. Chem., (2017), vol. 292, No. 25, pp. 10639-10650.
International Search Report dated Jul. 31, 2018 in International (PCT) Application No. PCT/JP2018/018346.

* cited by examiner

*Primary Examiner* — Nghi V Nguyen
(74) *Attorney, Agent, or Firm* — Wenderoth, Lind & Ponack, L.L.P.

(57) ABSTRACT

A β-1,6-glucanase mutant which is a mutant of β-1,6-glucanase (EC 3.2.1.75), wherein a Glu residue located at a position corresponding to Glu (E)-321 in SEQ ID NO: 1 is substituted by an amino acid residue X or a Glu (E) residue located at a position corresponding to each of Glu (E)-225 and Glu (E)-321 in SEQ ID NO: 1 is substituted by an amino acid residue X, wherein the amino acid residue (X) is selected from the group consisting of Gln (Q), Gly (G), Ala (A), Leu (L), Tyr (Y), Met (M), Ser (S), Asn (N), and His (H); and a method for measuring β-1,6-glucan, including measuring β-1,6-glucan bonded to the mutant.

10 Claims, 14 Drawing Sheets
Specification includes a Sequence Listing.

Fig. 13-1

| | | |
|---|---|---|
| S. degradans | MTLLKNINKQRLARKVRLVCSAISLYVNGFSGAASA----------------NQYKLTSGDLS | 47 |
| B. thetaiotaomicron | MINNRNIALT--------FLSCFTI--------LAACSNSDDAEKPVVPVPTGDVAIYTTTSSLT | 49 |
| L. edodes | ----MNSSQL--------SFLL--------LFV--------GPVAS----GGINDINGTTNDRS | 32 |
| N. crassa | ----------------------MYPPALTLLL----------------TPGLV---AAAIGPQAYASSAD | 29 |
| T. harzianum | ----MRYALI--------ASNLGGAAISVAMPS--------------EPAHS---PRAAGAQAYASNDA | 40 |
| A. fumigatus | ----MRIS-V--------GALLGLT--------ALS-----------HATTE---KRAASASAYCGNSA | 34 |
| | | |
| S. degradans | AAFEEGGEK--------YA-VA-PSPEMPLITIDKSDAFGTMEGFGYTLNGGSATNLANMSDA | 100 |
| B. thetaiotaomicron | RDLTRGAVN--------FS-PK-DNLAPTTITLNPAEQYQTMDGFGAAITGGTCYNLLLNKPA | 102 |
| L. edodes | GLFTSLAPSTPI-NFVSPGAIGSADIYVDD---GSVFQTVYGFGGSLTDSAAELLNNLKTT | 89 |
| N. crassa | GRYKLSSYGAPVRGTGTPGSNGTNKLTIDDTPSGRKGTIKGFGAAVTDSTYGGVFNALPSA | 89 |
| T. harzianum | SNYKLTSIAAPVGGNGSPGP-STNNLSIDDTSSGYKGKIVGFGAAVTDATVSAFNELSAS | 99 |
| A. fumigatus | GNYKLSSTAAPVQGAGNPGGESTNGLTVDDTSSGHKQTIVGFGAAVTDATVTSFNTLSAS | 94 |
| | | |
| S. degradans | AR----ARLLGEIFGGSDGANTNKPSIGVSYLRLSLGASDLQPAPFSYNDLPPGEVDLKLE | 157 |
| B. thetaiotaomicron | DR----HAFLTETFSDKD----------GFGFSYIRISIGCSDFSLSEYTGCDTK--------GIE | 146 |
| L. edodes | NSNNYNALLDYLFSPTDGAN--------AAGLNYIRVPLGASDFSAS-VYNYDCTSG---DTSFN | 142 |
| N. crassa | GR----TALLNTLNTPA--------GANFANNRHTIASSDLSANPAYSYDDGNDQTDLSLS | 138 |
| T. harzianum | TL----SQLLDELMTGA--------GASFSLNRHTIGASDLSGDPAYTYDDNGGNADPGMT | 148 |
| A. fumigatus | VL----QDLLNRLMTPA--------GANFALNRHTIGASDLSGDPAYTYDDNGGKADPSLS | 143 |
| | | |
| S. degradans | KFTIAQ-DEKTLIPILKGILAINPNITFNASPNGPPVNNKTNGS--------------T-------- | 201 |
| B. thetaiotaomicron | NFALGSEEKDYILPILKEILAINPSIKVIAAPNYCPKNNRYKSLTDRTPLDSN-------- | 199 |
| L. edodes | NFNINA-APSYVFSVLGDIKSVNGYLKIHVLPNSPPGNNKTSGSNDGGSLSSN-------- | 194 |
| N. crassa | NFNLGD-NSNANASLLAENNRLQPGLTILGSPNSPPGNNKLNRVIGGTTYNNNLDH------ | 193 |
| T. harzianum | GFNLGD-RGTAMATNLAGNKGLNSNLQIFGSPNSAPGNNNKLNNAIDGNTNNNNLNDGYLT | 207 |
| A. fumigatus | GFNLGD-RGTAMAKNLATNKSLGPNNLKILGSPNSAPGNNKLNGVLDGNTNNNNLNDGYLT | 202 |
| | | |
| S. degradans | IGGELNPEYYSVYAGYFVKYVGAMAEHGININDAITIGNEPNRPG-NNPSLLNHAKDGADF | 260 |
| B. thetaiotaomicron | TNGQLNPDYYQDYATYFVKNIGAFKAEGIDIYAVTPQNEPLNRG-NGASLYMENEEGRDF | 258 |
| L. edodes | --------EVTFYATYLFKSLGGFGSKGLTPYAISIGNEPQNSDTTYPSCTMSVAVEAQ- | 245 |
| N. crassa | --------AYASGFAGYFVKYLGAYGAKGANIDAITIGNEPLNSGRADMPTNYIYADEAGDL | 246 |
| T. harzianum | NNGA----QYSAAFAGYFVKYIGAFESHGATINAITLGNEPLNSGAGYPTMYNFSYEGGDL | 264 |
| A. fumigatus | SGGTGSTGYASQFAGYFVKYIGAYKNLGAHVDAITIGNEPLFSSAGYPTMYYYDYESAGDL | 262 |

| | | |
|---|---|---|
| S. degradans | IANRLGPAFK-----QAEL-KTKIIVNDHNAD--------KPEYPIEVLNHPVANQYIHGSAF | 309 |
| B. thetaiotaomicron | VKTALGPGNR-----AAGL-STKIYAFDHNYNYDNIESGKNYPGKIYEDAAASQYLAGAAY | 313 |
| L. edodes | -----IGNALRSNNNNNGFGAVKIIGFDHNNS-------GVSTYAIPLLQA--APNSFAGVAF | 294 |
| N. crassa | IQNNIGPALR-----NAGL-DTKIWAYDHNTD--------QPSYPATVLSR--AGGYVPAVAW | 393 |
| T. harzianum | IQNYVAPALK-----AAGL-STKIWAYDHNTD--------QPDFPEQVNGI---AADDVSAVAW | 311 |
| A. fumigatus | IQNYIGPALA-----SAGL-DTEIWAYDHNTD--------YPSYPQTVLNG--AGGYVKSVAW | 309 |
| | | |
| S. degradans | HLYGGDVNA---ISQYHNAHPDKHLYFTEQNVGANS----NFWGDVAMNIVENLIVGATRNNC | 364 |
| B. thetaiotaomicron | HNYGGNNEE--LLNIHGAYPEKELLFTETSIGTNNSGRDLSKRLMEDNNEEVALGTIANNNG | 371 |
| L. edodes | HCYEBTVSE---GAAFQTAFPNRE IYFTECIGSLG----SDWNSDIKNYMDNIFIGALSYGA | 349 |
| N. crassa | HCYASSLDNTVLTTFHNAHPGVEQYNTECNTSARGP-TPNNNAA-------SFTNGPLQNNA | 347 |
| T. harzianum | HCYATNLDNTVLTNFHNSYPNTDGYNTECNTPST----GANNGAA-------SFTNGPLQNNA | 363 |
| A. fumigatus | HCYAPNVDNTVLSQFHNTNPGVKQYNTECNTPAS----GANHGAA-------DFTNGPLQNNA | 361 |
| | ++ | |
| S. degradans | KTVLENNLAADSNLGPHFTL---GSCD-ACLGALTIDGGN-----VKRNAAYYIIAHAAKHVPP | 418 |
| B. thetaiotaomicron | KGVIVWNLNLDNDRGPNRE---GGCQ-TCYGAVDINNSDYKTIIRNSHYYIIAHLSSVVKP | 428 |
| L. edodes | STGLMWNLALDGNGNPFLPGSDSCGGSCGRGIVQIN-SDG-TYSYNGEFYSMAGASKAIIP | 407 |
| N. crassa | SGVTAWVLGTDTNDGPHLTGSDACG-KCTGLVWVDTAAG-TYNLRGDYYNNAQFSKFNRK | 405 |
| T. harzianum | RGVAANTLGTTAGDGPHLS-SGGCQ-TCTQLVTIN---NG-GYTFQTAYYNNAQFSKFNPY | 418 |
| A. fumigatus | SGVAANTLGTNAQDGPHLS-TGGCA-TGGGLYTIN---NG-GYTLNTAYYNNAQFSKFNPP | 416 |
| | | |
| S. degradans | GSVR------------IHSHR-------V---AGLPNVAFLT-PQKKVVVVVLNNTTQ-------LQS | 456 |
| B. thetaiotaomicron | GAVR------------IATTG-------YTDNGITCSAFER-TDGTYAFVLINNNEK-------SKK | 468 |
| L. edodes | KDVGSPFGGRIGVTIGGELSWALIVGAYV---TGRVNPTDNLRYSIVVLNNDDTNNGSNDP | 465 |
| N. crassa | GAV-------------VNSGTGSNTYGDGSGLESVAATNADDGSRVVVIENKF----GNEIVYT | 452 |
| T. harzianum | GAT-------------VLSGTGSYTYSGSGGVQSVASLN-PDGTRTVVIENTF----GNDIYIH | 464 |
| A. fumigatus | GAI-------------VLNGSGSYTYSGGGGIGSVASLN-PDGTRTVVIENTF----GNDVYVT | 462 |
| | | |
| S. degradans | FTLVH-----DNGKFAYSNPAGGVVTLVID----------------------- | 481 |
| B. thetaiotaomicron | ITVSD-----GGRHFAYDVPGKSVTSYRNAKSK------------------- | 496 |
| L. edodes | VAVPTTIEFRGNQASYTFPVGVTTLNNFASETSLNGTNAESYALYSETDGKQQPLHFFQ | 524 |
| N. crassa | VEAKSGEYNSG-------LYYRNSVYTNVLPAAGA----------------- | 480 |
| T. harzianum | LSTSSGQENSG-------NVPTNSVTTNVLPAV------------------- | 490 |
| A. fumigatus | VTNKSGGKNSG-------NAPSGSYTTNVLPSA------------------- | 488 |

ища # β-1, 6-GLUCANASE MUTANT, AND METHOD FOR MEASURING β-1, 6-GLUCAN

TECHNICAL FIELD

The present invention relates to a β-1,6-glucanase mutant that does not have a glucan cleavage activity but has a specific binding activity to β-1,6-glucan, and a method for measuring β-1,6-glucan using the β-1,6-glucanase mutant.

BACKGROUND ART

β-Glucan is a main polysaccharide constituting a fungal cell wall and is roughly divided into β-1,3-glucan, a polysaccharide in which glucose molecules are linked by β-(1→3) bonds, and β-1,6-glucan, a polysaccharide composed of β-(1→6) bonds. β-1,3-glucan is recognized by Dectin-1 on a mammalian cell membrane to induce an innate immune response, thereby promoting elimination of pathogenic fungi. In addition, β-1,3-glucan is recognized by a β-glucan recognition protein (βGRP) in insect bodies, such that elimination of fungi is promoted by an action of phenol oxidase. As described above, β-1,3-glucan exposed to fungal cell walls is an important factor for starting host immune responses.

In addition, a recognition system of β-1,3-glucan is applied in a medical field. Limulus factor G, a β-1,3-glucan recognition protein derived from horseshoe crabs, is used as an in-vitro diagnostic drug for detecting β-1,3-glucan in human blood (LAL method). A high value of β-1,3-glucan suggests a possibility of fungal infection. Currently, in clinical practice, a chromogenic synthetic substrate method (Fungitec G Test MK II Nissui: cut-off value of 20 pg/mL), (β-glucan Test Maruha: cut-off value of 11 pg/mL), and a turbidimetric analysis method (β-glucan test Wako: cut-off value of 11 pg/mL) are mainly used. Further, a β-glucan-binding protein derived from a factor G subunit a, which is a horseshoe crab blood cell component, and a method for measuring β-glucan using the same are known in Patent Literature 1.

CITATION LIST

Patent Literature

Patent Literature 1: PCT/JP 2010/054568
Patent Literature 2: JP 2003-149247 A

Non Patent Literature

Non Patent Literature 1: Uchiyama M, et. al., FEMS Immunol. Med. Microbiol., 1999 Jul. 15; 24(4): 411-20.
Non Patent Literature 2: St John F J, et. al., FEBS Lett., 2010 Nov. 5; 584(21): 4435-41.

SUMMARY OF INVENTION

Technical Problem

Not only β-1,3-glucan but also β-1,6-glucan is abundantly present in cell walls of fungi, and when the fungi are grown, a large amount of β-1,6-glucan is released to an external environment. β-1,6-glucan is not present in the body of a healthy person, such that β-1,6-glucan may become an indicator of fungal growth like β-1,3-glucan. Further, β-1, 3-glucan detected by a current LAL test is partially contained in some plant cell walls, and false positives in the LAL test are often problematic in hemodialysis patients using a dialysis membrane made of cellulose or the like, patients using medical gauze, or the like. Meanwhile, since β-1,6-glucan is not contained in plant cell walls, it can be expected to be an indicator that is unlikely to produce a false positive. In view of a ratio of β-1,3-glucan and β-1,6-glucan in exopolysaccharides, there are species in which a ratio of β-1,6-glucan is higher than that of β-1,3-glucan depending on fungal species such as *Candida albicans*, and the like (Non Patent Literature 1). In addition, since there are fungi in which polysaccharides constituting cell walls only contain β-1,6-glucan or hardly contain β-1,3-glucan (for example, Pustulan, Islandican, etc. as shown in Table 1 below), it is preferable to perform not only LAL test using β-1,3-glucan as an indicator but also detection of β-1,6-glucan at the time of diagnosing fungal infections. However, there were no coagulation factors specifically reacting with β-1,6-glucan, and thus, it was impossible to perform fungal infection diagnosis targeting β-1,6-glucan.

An object of the present invention is to provide a novel material having a specific binding activity to β-1,6-glucan, and a method for measuring β-1,6-glucan using the same.

Solution to Problem

The present inventors prepared a β-1,6-glucanase mutant in which an amino acid residue present in a catalytic enzyme region of β-1,6-glucanase, which is a β-1,6-glucan degrading enzyme, was substituted by another amino acid residue, and the present inventors found that the mutant in which a specific amino acid residue was substituted did not have a β-1,6-glucan cleavage activity and had a specific binding activity to β-1,6-glucan, thereby completing the present invention. In addition, the present inventors have made it easy to recognize a fungal exopolysaccharide (glyco-protein complex) by a labeled mutant obtained by adding a labeling substance to this β-1,6-glucanase mutant, thereby completing a measurement system to detect fungus-derived polysaccharide within a short period of time.

Further, as a mutant enzyme maintaining a substrate binding property while eliminating or decreasing a catalytic activity by substituting an amino acid residue present in a catalytic activity region of the enzyme with another amino acid residue, a cholesterol oxidase mutant disclosed in Patent Literature 2 has been known. In addition, with respect to a Glycoside Hydrolase Family 30 including β-1,6-glucanase, an amino acid residue constituting a catalytic activity region has been known (Non Patent Literature 2). However, in actually preparing of a mutant, as shown in the following Examples, even if an amino acid residue in a known β-1,6-glucanase degrading activity region was substituted to eliminate or decrease the degrading activity, a β-1,6-glucan binding property may not be maintained in a preferable state. Therefore, even though Patent Literature 2 and Non Patent Literature 2 are known, intensive research and development activities involving trial and error are required in order to obtain a β-1,6-glucanase mutant to be desired.

The present disclosure provides the following inventions as solution for solving the above-mentioned problems based on novel findings by the present inventors.

(1) A β-1,6-glucanase mutant E321X which is a mutant of β-1,6-glucanase (EC 3.2.1.75), wherein a Glu (E) residue located at a position corresponding to Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H).

(2) A β-1,6-glucanase mutant E225X/E321X which is a mutant of β-1,6-glucanase (EC 3.2.1.75), wherein a Glu (E) residue located at a position corresponding to each of Glu (E)-225 and Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H).

(3) A method for measuring β-1,6-glucan, including measuring β-1,6-glucan bonded to the β-1,6-glucanase mutant E321X described in the above (1) or the β-1,6-glucanase mutant E225X/E321X described in the above (2).

(4) A β-1,6-glucan measuring reagent containing the β-1,6-glucanase mutant E321X described in the above (1) or the β-1,6-glucanase mutant E225X/E321X described in the above (2).

(5) A β-1,6-glucan measuring reagent containing a labeled mutant E321X obtained by adding a labeling substance to the β-1,6-glucanase mutant E321X described in the above (1) or a labeled mutant E225X/E321X obtained by adding a labeling substance to the β-1,6-glucanase mutant E225X/E321X described in the above (2).

(6) A β-1,6-glucan measuring kit containing the reagent described in the above (4) and the reagent described in the above (5).

(7) The β-1,6-glucan measuring kit described in the above (6), wherein the β-1,6-glucanase mutant E321X and/or E225X/E321X are immobilized to an insoluble carrier.

Advantageous Effects of Invention

The present invention enables rapid and highly sensitive measurement of β-1,6-glucan that was impossible in the related art, such that diagnosis accuracy of fungal infection can be significantly improved. In addition, it becomes easy to determine the timing of continuation or termination of the antifungal drug administration by monitoring a concentration of β-1,6-glucan in the blood, such that an antifungal drug often causing side effects can be appropriately used.

BRIEF DESCRIPTION OF DRAWINGS

FIG. 8A shows an outline of the test. FIG. 8B is a result of the ELISA-like test using E321Q, and FIG. 8C is a result detected by the Limulus test.

FIG. 9A schematically shows genes of expressed E321Q-NL. FIG. 9B shows a result by separating purified E321Q-NL using SDS-PAGE and detecting E321Q-NL using CBB staining. FIG. 9C is a result obtained by detecting Pustulan corresponding to β-1,6-glucan and polysaccharides in a C. albicans culture supernatant (1000-fold dilution) using a biotinylated E321Q immobilized to magnetic beads and soluble E321Q-NL.

FIG. 10A is a result obtained by converting an amino acid located at a 321st position of β-1,6-glucanase to various amino acids, expressing it in E. coli, separating it by SDS-PAGE after purification, and detecting it by silver staining. FIG. 10B is a result obtained by a β-1,6-glucan (Pustulan) cleavage activity of various β-1,6-glucanase mutants by a Somogyi-nelson method using an increase in an amount of a reducing end as an indicator. FIGS. 10C and 10D are results obtained by measuring a Pustulan binding force of various β-1,6-glucanase mutants by biolayer interferometry. FIG. 10E is a result obtained by analyzing binding properties of various β-1,6-glucanase mutants with Pustulan by ELISA (direct method).

FIG. 11A schematically shows genes of expressed E321Q-SBP-1 and E321A-HiBiT. FIG. 11B shows a result obtained by separating E321Q-SBP1 and E321A-HiBiT by SDS-PAGE and detecting E321Q-SBP1 and E321A-HiBiT by silver staining. FIG. 11C is a result obtained by detecting Pustulan corresponding to β-1,6-glucan and polysaccharides in a C. albicans culture supernatant (1000-fold dilution) using E321Q-SBP1 immobilized on magnetic beads and soluble E321A-HiBiT.

FIG. 13 is an alignment diagram showing the corresponding homologous sequence regions of amino acid sequences of six kinds of β-1,6-glucanase (EC 3.2.1.75).

DESCRIPTION OF EMBODIMENTS

Figure 1:
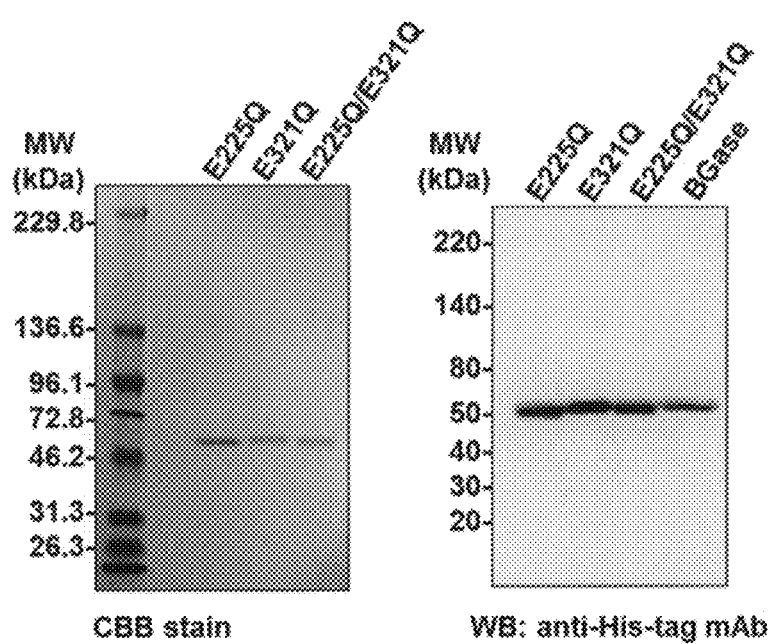
FIG. 1 is a result obtained by performing polyacrylamide gel electrophoresis of a β-1,6-glucanase mutant and detecting WB using (A) CBB staining or (B) an anti-His-Tag antibody.

A β-1,6-glucanase mutant E321X of the invention (1) is a mutant of β-1,6-glucanase (EC 3.2.1.75), and a Glu (E) residue located at a position corresponding to Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H). In addition, a β-1,6-glucanase mutant E225X/E321X of the invention (2) is also a mutant of β-1,6-glucanase (EC 3.2.1.75), and a Glu residue located at a position corresponding to each of Glu (E)-225 and Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H). That is, Glu (E) at a predetermined position is substituted by any one of these amino acid residues X, such that an enzymatic activity of the β-1,6-glucanase mutant is eliminated or decreased, and at the same time, a β-1,6-glucan binding property is maintained in a preferable state. As the amino acid residue X, Gln (Q), Gly (G), Ala (A), Asn (N), and Ser (S) are more preferable in view that the β-1,6-glucan binding property is good, and Gln (Q), Gly (G), and Ala (A) are particularly preferable.

In the present invention, the phrase "the Glu (E) residue located at a position corresponding to Glu (E)-321 in SEQ ID NO: 1" means as follows. That is, as an example, FIG. 13 shows a homologous sequence region of amino acid sequences (GenBank Accession numbers; AAO78418.1, ABD82251.1, EAL85472.1, BAK52530.1, BAB91213.1, CAC80492.1) of β-1,6-glucanase (EC 3.2.1.75) derived from *Bacteroides thetaiotaomicron*, *Saccharophagus degradans*, *Aspergillus fumigatus*, *Lentinula edodes*, *Neurospora crassa*, and *Trichoderma harzianum*. Further, as a representative of the entire amino acid sequence, an amino acid sequence of β-1,6-glucanase derived from *Neurospora crassa* is shown in SEQ ID NO: 1. As shown in FIG. 13, as an active site of each β-1,6-glucanase, there is a common sequence QNEP (marked with *) as an acid/base located in the vicinity of an N-terminus and a common sequence TE (marked with +) as a nucleophile located in the vicinity of a C-terminus. In the β-1,6-glucanase mutant of the invention, E in these common sequences QNEP and TE is substituted by any one of the amino acid residues X. As a common substituted amino acid residue E described above, E located at the position corresponding to Glu (E)-321 in SEQ ID NO: 1 is defined. The same applies to "Glu (E) at the position corresponding to Glu (E)-225 of SEQ ID NO: 1 in the invention (2)". Specifically, in the case of the β-1,6-glucanase mutant derived from *Bacteroides thetaiotaomicron*, E-339, and E-238 and E-339 are substituted with the amino acid residue X; in the case of the β-1,6-glucanase mutant derived from *Saccharophagus degradans*, E-335, and E-240 and E-335 are substituted with the amino acid residue X; in the case of the β-1,6-glucanase mutant derived from *Lentinula edodes*, E-320, and E-225 and E-320 are substituted with the amino acid residue X; in the case of the β-1,6-glucanase mutant derived from *Trichoderma harzianum*, E-339, and E-243 and E-339 are substituted with the amino acid residue X; and in the case of the β-1,6-glucanase mutant derived from *Aspergillus fumigatus*, E-337, and E-241 and E-337 are substituted with the amino acid residue X.

The β-1,6-glucanase mutant of the present invention is not limited to the six types characterized above. For example, as long as β-1,6-glucanase is an endo-β-1,6-glucanase (BGase) (EC 3.2.1.75) registered in Glycoside Hydrolase Family 30 Subfamily 3 of carbohydrate-related enzyme database CAZy (www.cazy.org/), the β-1,6-glucanase mutant can be prepared by substituting E located at a predetermined position by the amino acid residue X based on an amino acid sequence thereof.

The β-1,6-glucanase mutant of the present invention can be prepared, for example, by the following method. SEQ ID NO: 1 is a known amino acid sequence (GenBank/ BAB91213.1) of Endo-β-1,6-glucanase (EC 3.2.1.75) (GH30_3) (BGase) of red bread mold (*Neurospora crassa*; NBRC 6068). The β-1,6-glucanase mutant E321X of the invention (1) can be prepared, for example, by preparing a mutant DNA in which a codon corresponding to an amino acid residue Glu-321 in DNA encoding an amino acid sequence of the β-1,6-glucanase (for example, β-1,6-glucanase CDS (region of base numbers 46966-48408) of *Neurospora crassa* DNA described in GenBank: BX908809.1) is substituted with a codon of the amino acid residue X, and expressing this mutant DNA by genetic engineering. Similarly, the β-1,6-glucanase mutant E225X/E321X of the invention (2) can be prepared by expressing a mutant DNA in which a codon corresponding to each of the amino acid residues Glu-225 and Glu-321 amino acids is substituted by a codon of the amino acid residue X.

In the method for measuring β-1,6-glucan of the invention (3) is, for example, the β-1,6-glucanase mutant E321Q described in the invention (1) or the β-1,6-glucanase mutant E225Q/E321Q described in the invention (2) is brought into contact with a test sample to form a complex of the mutant E321Q or the mutant E225Q/E321Q and β-1,6-glucan in the test sample, and the presence of the complex is detected or an amount of the complex is quantified. Such a measurement can be performed according to, for example, a direct adsorption method, a sandwich method, a competition method, etc., in a known ELISA method, but particularly, a sandwich method or a competition method by a combination of the mutant E321Q and a labeled mutant E321Q, or a combination of the mutant E225Q/E321Q and a labeled mutant E225Q/E321Q is preferable. The contents disclosed in Patent Literature 1 can be adopted for these specific procedures, labeling substances, the kind of carrier, and the like.

Hereinafter, the present invention can be described in more detail concretely through Examples, but the present invention is not limited to the following Examples.

EXAMPLES

Example 1: Preparation of β-1,6-Glucanase Mutant

A gene sequence encoding β-1,6-glucanase from cDNA of red bread mold (*Neurospora crassa* NBRC 6068) was amplified by PCR according to the previous report (Oyama S, et. al., Biosci. Biotechnol. Biochem., 2002 June; 66(6): 1378-81), and an amino acid residue [glutamic acid (Glu (E)]-225 and/or Glu (E)-321 in an amino acid sequence of SEQ ID NO: 1] controlling an enzymatic activity was substituted by glutamine (Gln: Q). This modified gene sequence of the enzyme was inserted into a pColdI vector (manufactured by Takara Bio Inc.), transformed into *Escherichia coli* Shuffle (manufactured by New England Biolabs), and massively expressed in an ampicillin-added LB medium as a 6× histidine tag (His-Tag)-fused protein. After purification using TALON® Metal Affinity Resin (manufactured by Takara Bio Inc.), the presence of the purified protein was confirmed by SDS-PAGE (FIG. 1). A β-1,6-glucanase mutant in which Glu (E)-225 of SEQ ID NO: 1 was substituted by Gln (Q) was designated as E225Q, a β-1,6-glucanase mutant in which Glu (E)-321 was substituted by Gln (Q) was designated as E321Q, and a β-1,6- glucanase mutant in which both Glu (E)-225 and Glu (E)-321 were substituted was designated as E225Q/E321Q.

Figure 2:
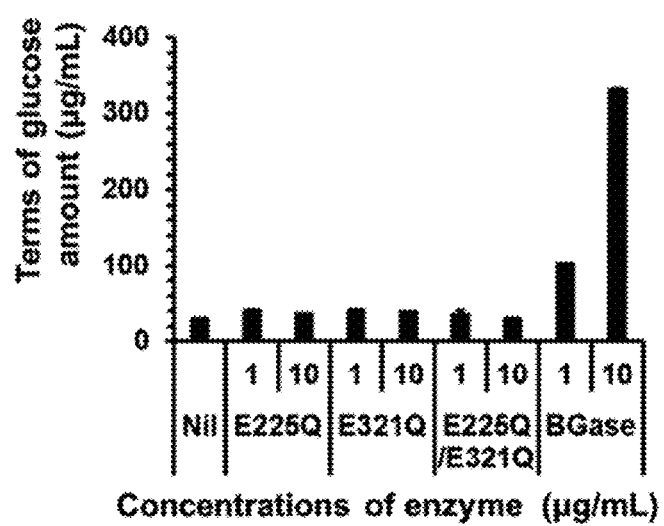
FIG. 2 is a result obtained by measuring a β-1,6-glucan cleavage activity of the β-1,6-glucanase mutant by a Somogyi-nelson method using an increase in an amount of reducing end of Pustulan as an indicator.

Example 2: β-1,6-Glucan Cleavage Activity and Binding Activity of β-1,6-Glucanase Mutant After mixing natural β-1,6-glucanase (BGase) and respective mutants E225Q, E321Q, and E225Q/E321Q (each 1 or 10 μg/mL) with Pustulan (1 mg/mL) (derived from *Umbilicaria papullosa*, manufactured by Calbiochem., water-soluble fraction) corresponding to β-1,6-glucan in a 50 mM acetate buffer (pH 6.0) and performing a reaction at 37° C. for 1 hour, an amount of a reducing end formed by cleavage was measured by a Somogyi-Nelson method. As a result, the BGase showed an increase in the amount of the reducing end depending on an addition concentration of the protein, whereas none of the mutants E225Q, E321Q, and E225Q/E321Q showed cleavage activity against β-1,6-glucan (FIG. 2).

Next, β-1,3-glucan Laminarin (manufactured by Sigma) and β-1,6-glucan, that is, Pustulan, were each dissolved in a 100 mM Carbonate buffer (pH 9.5) at a concentration of 0 to 5000 ng/mL, coated on an ELISA plate (manufactured by Greiner Bio-One), and allowed to stand overnight at 4° C. After the ELISA plate was washed with PBS to which 0.05% Tween 20 (manufactured by Wako) was added (that is, PBST), PBST to which 1% BSA (manufactured by Sigma) was added (that is, BPBST) was added to the plate and reacted at room temperature for 1 hour, thereby blocking the ELISA plate. Subsequently, each of the mutants E225Q, E321Q, and E225Q/E321Q was diluted with BPBST so as to have a final concentration of 2 ug/mL, and then added to the washed ELISA plate. After performing a reaction at room temperature for 1 hour and washing, an HRP-conjugated His-Tag antibody (manufactured by BioLegend) diluted with BPBST was added to each well, and a reaction was carried out again for 1 hour. After sufficiently washing the resultant with PBST, a TMB solution (manufactured by KPL) was added thereto as an HRP substrate, a reaction was carried out at room temperature, a reaction stop solution (1N phosphoric acid) was added thereto, and then absorbance (measurement wavelength: 450 nm/control wavelength: 630 nm) was measured using a microplate reader.

Figure 3:
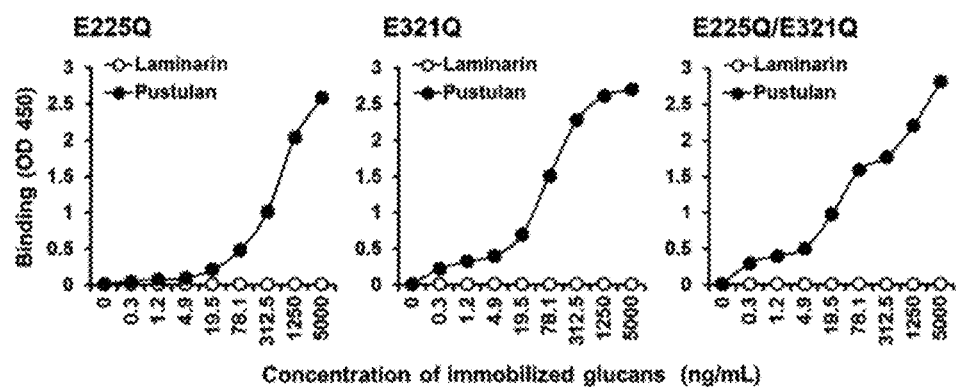
FIG. 3 is a result obtained by measuring a β-1,6-glucan binding activity of the β-1,6-glucanase mutant using an ELISA-like test.

As a result, each of the mutants E225Q, E321Q, and E225Q/E321Q showed strong binding ability to Pustulan (β-1,6-glucan) but did not show binding ability to Laminarin (β-1,3-glucan) (FIG. 3). In addition, in a well coated with low-concentration Pustulan, the mutants E321Q and E225Q/E321Q showed higher reactivity than the mutant E225Q. Meanwhile, in a well coated with high-concentration Pustulan, the mutant E321Q showed a strong absorbance, but the mutant E225Q and the mutant E225Q/E321Q had a slight decrease in absorbance. From these results, it was confirmed that the mutant E321Q and the mutant E225Q/E321Q were suitable as a β-1,6-glucanase mutant for measuring β-1,6-glucan, and the mutant E321Q was preferable in order to measure β-1,6-glucan in a wider concentration range.

Example 3: Thermal and pH Stability of β-1,6-Glucanase Mutant E321Q

Figure 4:
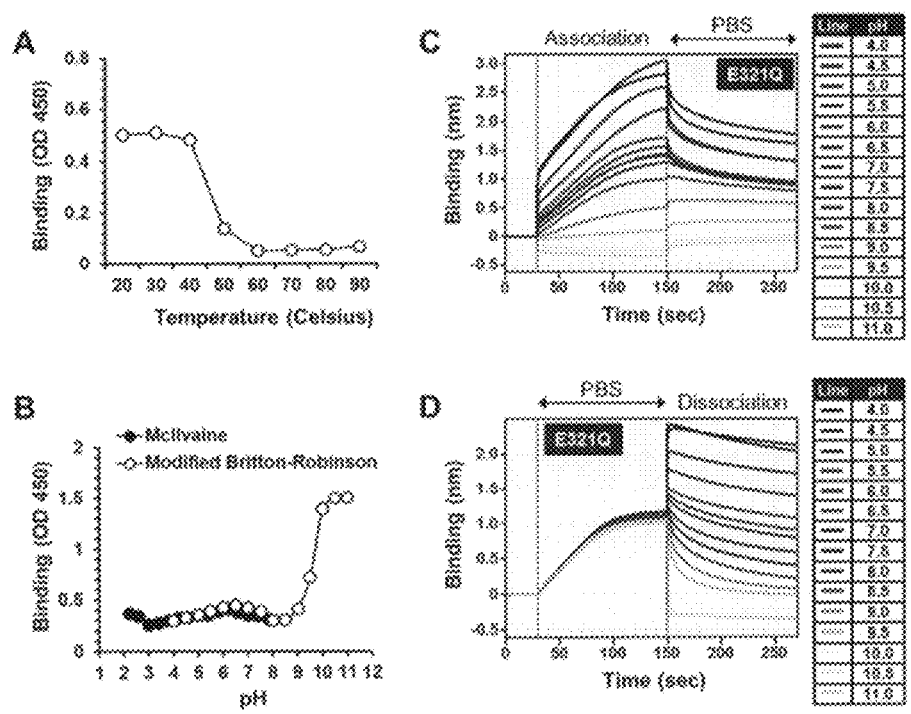
FIG. 4A is a result obtained by evaluating temperature stability of a β-1,6-glucanase mutant E321Q.
FIG. 4B is a result of evaluating pH stability of the β-1,6-glucanase mutant E321Q.
FIGS. 4C and 4D are results of detailed analysis of pH stability of the β-1,6-glucanase mutant E321Q by biolayer interferometry.

After the mutant E321Q diluted with PBS was dispensed into microtubes, treated at respective temperatures in a range of 20 to 90° C. for 5 minutes, and diluted with BPBST (0.5 μg/mL), binding ability to Pustulan (500 ng/mL, immobilized) was evaluated according to the ELISA method of Example 2. As a result, it was revealed that the mutant E321Q had stability up to 40° C., and β-1,6-glucan binding activity was eliminated by treatment at 50° C. or more (FIG. 4A).

Further, in a process of reacting Pustulan (500 ng/mL) coated on the plate with the mutant E321Q at the time of performing the ELISA method, the mutant E321Q was diluted (0.5 ug/mL) with a McIlvaine solution or modified Britton-Robinson solution, and β-1,6-glucan binding properties under various pH conditions (pH 2.2 to 11) were evaluated. As a result, the mutant E321Q showed relatively stable reactivity up to around pH 2.2 to 9 (FIG. 4B). However, since the reaction became unstable at pH 9 or higher, detailed analysis of a ligand-protein interaction was attempted by biolayer interferometry. Pustulan (500 nM) modified with biotinylated reducing end was immobilized on a streptavidin chip (manufactured by Pall ForteBio), a binding and dissociation reaction with the mutant E321Q (38.5 nM) in the modified Britton-Robinson solution under each pH condition was calculated using BLItz (manufactured by Pall ForteBio). As a result, it was confirmed that the binding ability of E321Q to Pustulan was significantly decreased under the condition of pH 9.0 or higher (FIG. 4C), and a dissociation rate increased with increasing pH (FIG. 4D), which suggested that an optimum pH for ligand-protein interaction in binding and dissociation was around 5.0 to 6.0. From these results, it was confirmed that in order to perform stable quantification of β-1,6-glucan, it is preferable to construct a measurement system in a buffer near pH 5 to 8, more preferably around pH 5 to 6.

Example 4: Reaction Characteristics of β-1,6-Glucanase Mutant E321Q

Figure 5:
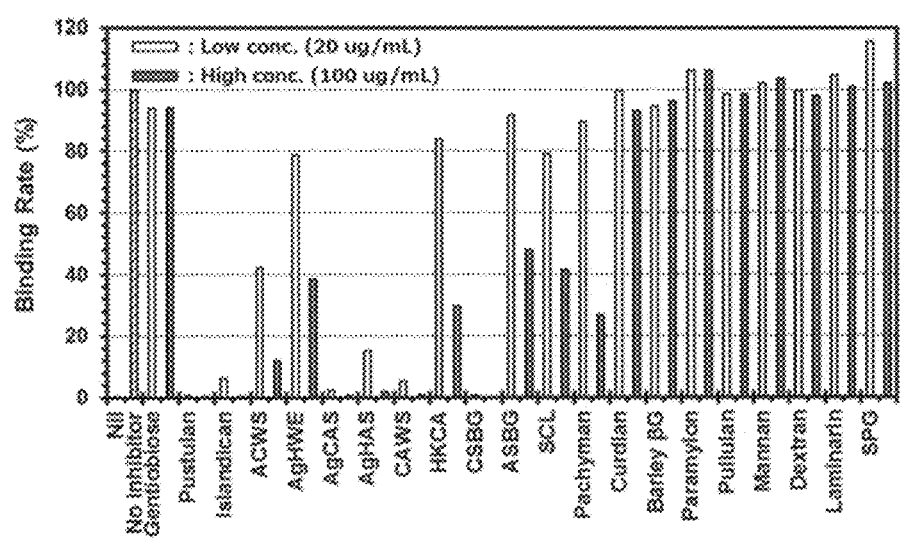
FIG. 5 is a result obtained by evaluating reactivity of the β-1,6-glucanase mutant E321Q with various β-1,6-glucans by a competitive ELISA-like test using a Pustulan-coated ELISA plate.

A mutant E321Q (0.5 ug/mL) previously mixed with various glucans (20 or 100 ug/mL) was added to an ELISA plate coated with Pustulan (500 ng/mL) according to the ELISA method of Example 2, and reactivity between various glucans and the mutant E321Q was evaluated by a competitive ELISA method. Various glucans used in the reaction are shown in Table 1, and references thereof are shown in Table 2. The mutant E321Q showed reactivity only with samples containing long-chain β-1,6-glucan (Pustulan, Islandican, ACWS, AgHWE, AgCAS, AgHAS, CAWS, HKCA, CSBG, ASBG, SCL, Pachyman, etc.), but reactivity of the mutant E321Q with glucan without β-1,6-glucan (Curdlan, Barley βG, Paramylon, Pullulan, Mannan, Dextran, etc.) or β-1,3-glucan with β-1,6-glucan monoglycoside linkage (Laminarin, SPG, etc.) was not observed (FIG. 5). In addition, reactivity with Gentiobiose in which two β-1,6-glucans were linked was not observed, and it was estimated that when a predetermined number of glucose molecules were not β-1,6-linked, the mutant E321Q did not bind thereto. These results suggest that the β-1,6-glucanase mutant E321Q reacts specifically with high-molecular weight β-glucan present in the blood and a non-specific reaction (false positive) is unlikely to occur.

TABLE 1

| No. | Abbreviation | Name of polysaccharide | Sources | MW | Structure | Distributor |
|---|---|---|---|---|---|---|
| 1 | Gentiobiose | Gentiobiose | — | 342 | β1,6 | Tokyo Chemical Industro Co., Ltd. |
| 2 | Pustulan | Pustulan | *Umbilicaria papullosa* | 20,000 | β1,6 | Calbiochem |
| 3 | Islandican | Islandican | *Penicillium islandicum* | — | β1,6 | Original |
| 4 | ACWS | *Agaricus blasiliensis* cold water-soluble fraction | *Agaricus blasiliensis* KA21 | — | β1,6 | Original |
| 5 | AgHWE | *Agaricus blasiliensis* hot water extract | *Agaricus blasiliensis* KA21 | — | β1,6/β1,3 | Original |
| 6 | AgCAS | *Agaricus blasiliensis* cold alkaline-soluble fraction | *Agaricus blasiliensis* KA21 | — | β1,6/β1,3 | Original |
| 7 | AgHAS | *Agaricus blasiliensis* hot alkaline-soluble fraction | *Agaricus blasiliensis* KA21 | — | β1,6/β1,3 | Original |
| 8 | CAWS | *Candida albicans* water-soluble mannoprotein-beta-glucan complex | *Candida albicans* NBRC1385 | — | β1,3/β1,6/mannan | Original |
| 9 | HKCA | Heat-killed *Candida albicans* yeast | *Candida albicans* NBRC1385 | — | β1,3/β1,6/mannan | Original |
| 10 | CSBG | *Candida* solubilized βG | *Candida albicans* NBRC1385 | — | β1,3/β1,6 | Original |
| 11 | ASBG | *Aspergillus* solubilized βG | *Aspergillus niger* NBRC6342 | — | α1,3/β1,3/β1,6 | Original |
| 12 | SCL | Scleroglucan | *Sclerotium folfsii* | 1,560,000 | β1,3/β1,6 (3:1) | CarboMer, Inc. |
| 13 | Pachyman | Pachyman | *Porio cocos* | 200,000 | β1,3 (β1,6) | Calbiochem |
| 14 | Cardlan | Cardlan | *Alcaligenes faccalis* var. *mycogenes* | 90,000 | β1,3 | Wako Pure Chemical Industries, Ltd. |
| 15 | Barley βG | Barley glucan | *Hordeum vulgare* | — | β1,3/β1,4 | Sigma |
| 16 | Paramylon | Paramylon | *Euglena cracilis* | 500,000 | β1,3 | Wako Pure Chemical Industries, Ltd. |
| 17 | Pullulan | Pullulan | *Aureobasidium pullulans* | 100,000 | α1,4/α1,6 (2:1) | Pfanstiehl Laboratories inc |
| 18 | Mannan | Mannan | *Saccharomyces cerevisiae* | — | α1,2&α1,3 mannan | Sigma |
| 19 | Dextran | Dextran T500 | *Leuconostoc mesenteroides* | 500,000 | α1,4/α1,6 | Pharmacia Fine Chemicals |
| 20 | Laminarin | Laminarin | *Laminaria digitata* | 3-6,000 | β1,3/β1,6 (7:1) | Sigma |
| 21 | SPG | Schizophyllan | *Schizophyllum commune* | 450,000 | β1,3/β1,6 (3:1) | Kaken Pharmaceutical Co., Ltd. |

TABLE 2

| No. | References |
|---|---|
| 1 | — |
| 2 | Sathyanarayaon, B. K., et al. "Theoretical study of the conformations of pustulan [(1-6)-beta-D-Glucan]." *J Biomol Struct Dyn.* [(4): 947-59 (1983) |
| 3 | Miyazaki, T., et al. "An endo-(1 lead to 6)-beta-D-glucanase from *Mucor hiemalis*." *Carbohydr Res.* 48(2): 209-16 (1976) |
| 4 | Yamanaka, D., et al. "Effect of *Agaricus brasiliensis*-derived cold water extract on Toll-like receptor 2-dependent cytokine production in vitro."*Immunopharmacol Immunoioxicol.* 34(4): 561-70 (2011) |
| 5 | Yamanaka, D., et al. "*Agaricus brasiliensis*-derived beta-glucans exert immunoenhancing effects via a dectin-1-dependent pathway."*Int Immunopharmacol.* 14(3):311-9 (2012) |
| 6 | Yamanaka, D., et al. "*Agaricus brasiliensis*-derived beta-glucans exert immunoenhancing effects via a dectin-1-dependent pathway."*Int Immunopharmacol.* 14(3):311-9 (2012) |
| 7 | Yamanaka, D., et al. "*Agaricus brasiliensis*-derived beta-glucans exert immunoenhancing effects via a dectin-1-dependent pathway."*Int Immunopharmacol.* 14(3):311-9 (2012) |
| 8 | Ohno, N. "Chemistry and Biology of Angiitis Inducer, *Candida albicans* Water-Soluble Mannoprotein-β-Glucan Complex (CAWS)" *Microbiol Immunol.* 47(7): 479-90 (2003) |
| 9 | — |
| 10 | Ohno N., et al. "Solubilization of yeast cell-wall beta-(1->3)-D-glucan by sodium hypochlorite oxidation and dimethyl sulfoxide extraction." *Carbohydr Res.* 316(1-4): 161-172 (1999) |
| 11 | Ishibashi, K., et al. "The solubilization and biological activities of Aspergillus beta-(1->3)-D-glucan." *FEMS Immunol Med Microbiol.* 1; 42(2): 156-66 (2004) |
| 12 | Pretus H A., et al. "Isolation, physicochemical characterization and preclinical efficacy evaluation of soluble scleroglucan."*J Pharmacol Exp Ther.* 257(1): 500-10 (1991) |
| 13 | Hoffmann G C., et al. "Structure and molecular size of pachyman." *Carbohydr Res.* 20(1): 185-8. (1971) |
| 14 | Harada T., et al. "Production of a firm, resilient gel-forming polysaccharide by a mutant of Alcaligenes Faecalis var. myxogenes 10 C3" *Agric Biol Chem* 30: 196-198 (1966) |
| 15 | Bacic A. "chemistry and organization of aleurone cell wall components from wheat and barley." *Aus J Plants Physiol.* 8: 475-95 (1981) |
| 16 | Clarke A E., Stone B A. "Structure of the paramylon from *Euglena gracilis*." *Biochem Biophys Acta.* 21; 44: 161-3(1960) |

TABLE 2-continued

| No. | References |
|---|---|
| 17 | Catley B I, Whelan W J. "Observations on the structure of pullulan." *Arch Biochem Biophys.* 143(1): 138-42 (1971) |
| 18 | Nagase, T., et al, "Lethal effect of neutral mannan fraction of bakers' yeast in mice." *Microbiol Immunol.* 28(9): 997-1007 (1984) |
| 19 | Ball, A., et al. "On the molecular weight distribution of dextran T-500."*Gums Stab. Food Ind. 5, [Proc. Int. Conf.],* 5th: 447-50 (1990) |
| 20 | Saito H., et al. "A high-resolution solid-state 13C NMR study of (1→3)-β-D-glucans from various sources. Conformation characterization as viewed from the conformation-dependent 13C chemical shifts and as consequence to gelation property. *Bull. chem. Soc. Jpn.* 59: 2019-2101 (1986) |
| 21 | Tabuta, K., "Ultrasonic degradation of schizophyllan, an antitumor polysaccharide produced by *Schizophyllum commune* Fries." *Carbohydr Res.* 16; 89(1): 121-35 (1981) |

Example 5: Highly-Sensitive Detection of β-1,6-Glucan

Figure 6:
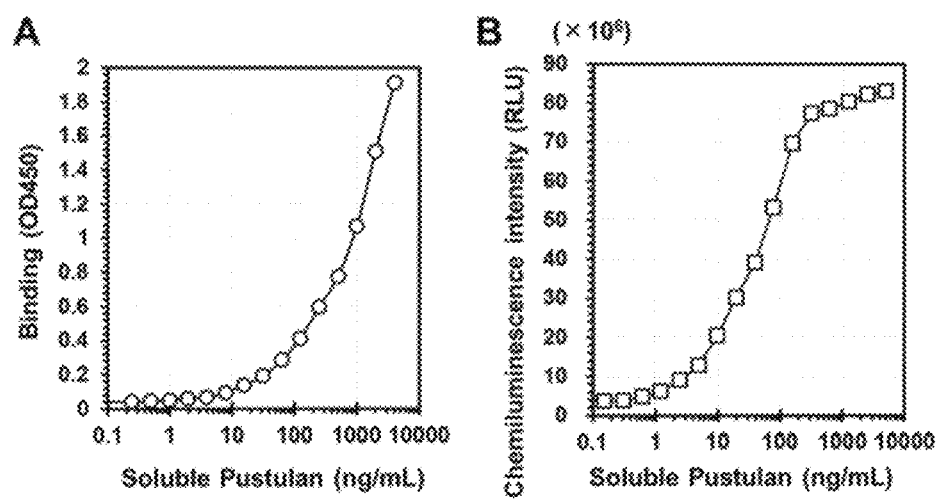
FIG. 6 is a result obtained by measuring soluble Pustulan by a sandwich ELISA-like test using an unlabeled β-1,6-glucanase mutant E321Q and a biotin-labeled E321Q, respectively.

The mutant E321Q was biotin-labeled with a commercially available biotinylation reagent (manufactured by DOJINDO: product code B306). First, after unlabeled E321Q (2 ug/mL) was coated on an ELISA plate and blocked with BPBST, Pustulan (0 to 4000 ng/mL) diluted stepwise with BPBST was added thereto and allowed to react at room temperature for 1 hour. After washing with PBST, biotinylated E321Q (1 ug/mL) diluted with BPBST was added thereto and allowed to react at room temperature for 1 hour, and then, after washing, streptavidin-HRP (manufactured by BioLegend) diluted with BPBST was added thereto. After 30 minutes, a TMB solution was added thereto after sufficient washing to develop a color appropriately. A reaction stop solution (1N phosphoric acid) was added thereto, and absorbance (measurement wavelength 450 nm/control wavelength 630 nm) was measured using a microplate reader. As a result, it was possible to measure a concentration of soluble Pustulan (about 10 to 4000 ng/mL) by a sandwich ELISA-like test of unlabeled E321Q and biotinylated E321Q (FIG. 6A). In order to realize detection with higher sensitivity, the above test was performed using a black plate for ELISA (manufactured by Greiner Bio-One). Immunostar® (manufactured by Wako) or SuperSignal™ ELISA Pico/Femto Substrate (manufactured by Thermo Fisher Scientific) was used to detect HRP, and GloMax® (manufactured by Promega) was used as a detector. As a result, a measurement range was expanded as compared to the conventional absorbance measurement methods, and it was possible to quantify about 0.6 to 5000 ng/mL of soluble Pustulan (FIG. 6B).

Figure 7:
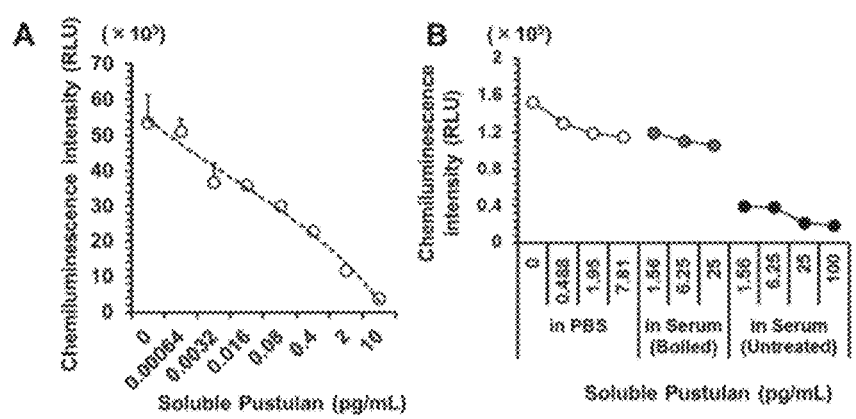
FIG. 7 is a result of highly sensitive detection of Pustulan with high sensitivity by a competitive ELISA-like test using a Pustulan-coated ELISA plate and a biotinylated β-1,6-glucanase mutant E321Q.

However, the sandwich ELISA method described above was not suitable for measuring even lower concentrations of Pustulan. Therefore, in order to further improve the detection sensitivity, a competitive ELISA-like β-1,6-glucan measurement was performed. Pustulan (500 pg/mL) was coated on a white plate for ELISA (manufactured by Greiner Bio-One), and the plate was washed after blocking. Biotin-labeled E321Q diluted with BPBST (final concentration: 100 ng/mL) and various concentrations of Pustulan were mixed and reacted at room temperature for about 1 hour, and then added to the plate. The reaction was carried out at room temperature for 1 hour, and after washing, streptavidin-HRP was added thereto, and washing was performed sufficiently after about 30 minutes. SuperSignal™ ELISA Pico/Femto Substrate was used for detection, and a luminescence level was measured using GloMax®. As a result, β-1,6-glucan detection of 1 pg/mL or less was achieved by the competition method (FIG. 7A). In addition, as a result of dissolving Pustulan in the human serum (manufactured by Sigma) and performing the same test, detection equivalent to that obtained by dissolving in PBS was possible by heating the serum at 98° C. for 10 minutes (FIG. 7B).

Figure 8:
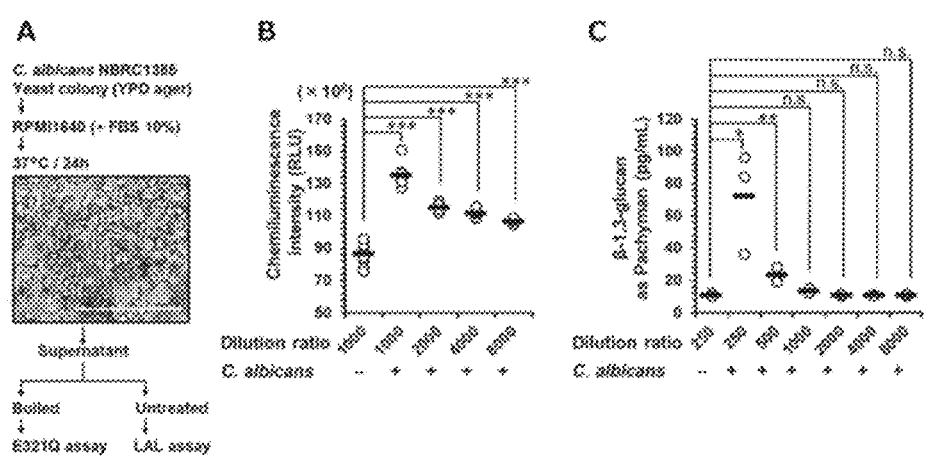
FIG. 8 is a result obtained by detecting β-glucan in a supernatant obtained by culturing Candida albicans for 24 hours using a serum-supplemented medium by a sandwich ELISA-like test or Limulus test using a β-1,6-glucanase mutant E321Q.

Example 6: Highly-Sensitive Detection of β-Glucan in Fungal Culture Supernatant and Comparison with Limulus Test Method β-glucan in a culture supernatant of a serum-added medium of *Candida albicans*, which is often a clinical problem, was measured by an ELISA test using the mutant E321Q. A *C. albicans* NBRC1385 strain (NITE) was pre-cultured on YPD agar medium, the formed colonies are suspended in D-PBS, and $1 \times 10^{\textasciicircum}6$ of *C. albicans* was inoculated in a 10% FBS-containing RPM11640 liquid medium (Gibco) (10 mL) and cultured at 37° C. for 24 hours (FIG. 8A). A supernatant containing no *C. albicans* was collected, and some of the supernatant was heated at 80° C. for 5 minutes and measured by a sandwich ELISA-like test (similar to the test using SuperSignal™ ELISA Femto Substrate in Example 5 except that a white plate was used as the plate) using E321Q. Further, some of the supernatant was analyzed by a Limulus test (Fangitek MKII) without heating. As a result, in the ELISA method using E321Q, detection was possible even after 2000-fold or higher dilution (FIG. 8B). On the other hand, in the LAL method, detection was possible up to 500-fold dilution, but detection was not possible in the case of 1000-fold or higher dilution (FIG. 8C).

Figure 9:
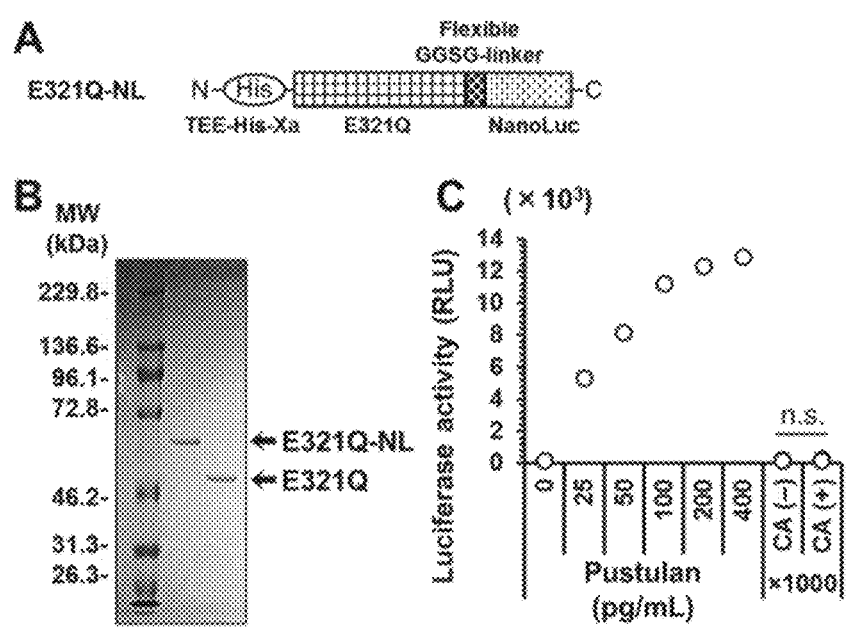
FIG. 9 is a result of highly sensitive detection of purified β1-,6-glucan by a sandwich ELISA-like test with β-1,6-glucanase mutant E321Q fused with NanoLuc and immobilized on an insoluble carrier.

Example 7: Rapid Detection of β-1,6-Glucan Using Insoluble Carrier and Luciferase-Fused E321Q In Example 6, β-glucan was successfully detected with high sensitivity from the pathogenic fungal culture supernatant, but there was a disadvantage in that it took several hours for detection. In order to shorten the time for detection, biotinylated E321Q was bonded to streptavidin-labeled magnetic beads (manufactured by Veritas Corp.). Again, NanoLuc (Promega), a small luciferase, was fused to E321Q, and expressed using *E. coli* (to prepare E321Q-NL), and the presence of E321Q-NL was confirmed by SDS-PAGE (CBB staining) (FIGS. 9A and 9B). Standard β-1,6-glucan (Pustulan) and E321Q-NL were diluted in BPBST, respectively, and a fungal culture supernatant (CA (+)) or a fungus-free blank solution (CA (−)) was heated at 80° C. for 5 minutes, and then, diluted 1000 times with BPBST and used for this test. A 96-well white plate (manufactured by Thermo Scientific) was previously blocked with BPBST, magnetic beads (5 µg) to which biotinylated E321Q (50 ng)

was immobilized were added to each well, Pustulan or *C. albicans* culture supernatant (CA (+)) or the blank solution (CA (−)) was added thereto and sufficiently stirred, and then, the magnetic beads were fixed with a magnetic separator (manufactured by Luminex) and washed with BPBST. Subsequently, by performing the same washing and adding Furimazine (manufactured by Promega), a luciferase substrate, after adding soluble E321Q-NL (0.1 ng) thereto and stirring, β-1,6-glucan was detected with high sensitivity within approximately 30 minutes (FIG. 9C). However, although this test method made it possible to detect Pustulan, purified β-1,6-glucan, it was difficult to detect sugar-protein complexes in the fungal culture supernatant (FIG. 9C). Therefore, it was confirmed that although this method was excellent for detection of purified β-1,6-glucan, the Nano-Luc-fused E321Q was not suitable for detection of an extracellular released polysaccharide having a complicated structure.

Example 8: Preparation of β-Glucanase Mutant with High Affinity Activity

Figure 10:
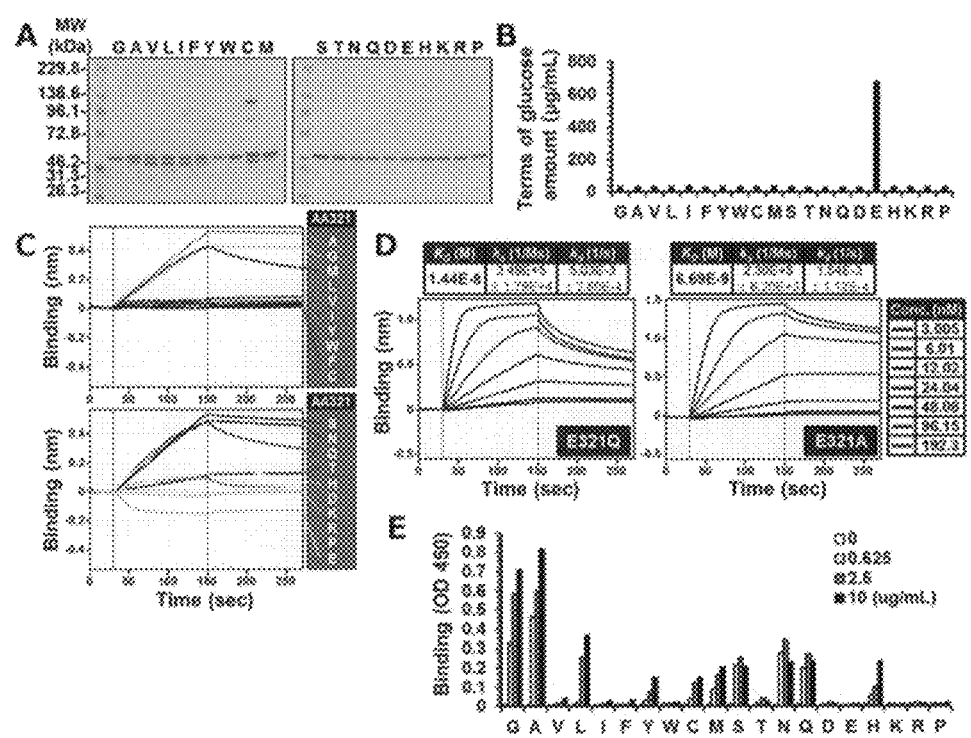
FIG. 10 is a result obtained by preparing various β-1,6-glucanase mutants and comparing binding activities thereof with Pustulan corresponding to a ligand by an ELISA-like test and biolayer interferometry.

In order to enhance a binding activity of the β-glucanase mutant to β-1,6-glucan, Glu (E)-321, a nucleophilic catalytic group, was converted to other amino acids, similarly expressed in *E. coli* and purified, a protein concentration was unified after purification, and its presence was confirmed by SDS-PAGE (silver staining) (FIG. 10A). It was proved by the Somogyi-Nelson method using an amount of a reducing end as an indicator that mutants other than the natural β-glucanase did not have a β-1,6-glucan (Pustulan) cleavage ability (FIG. 10B). Meanwhile, the binding ability to β-1,6-glucan was evaluated by an ELISA-like test in which Pustulan was immobilized based on the biolayer interference method using a streptavidin sensor chip (manufactured by Pall ForteBio) to which biotinylated Pustulan was immobilized or the ELISA method of Example 2. A sugar chain binding strength of each mutant (1 μg/mL) varied greatly depending on the kind of converted amino acids, and Gln (Q), Gly (G), Ala (A), Leu (L), Tyr (Y), Met (M), Ser (S), Asn (N), and His (H) showed binding ability, but in the case of substitution with the other amino acids, no strong binding ability was observed (FIG. 10C). Furthermore, a KD value indicating the affinity to a ligand showed a different value depending on the kinds of converted amino acids, and an enzyme mutant showing the strongest affinity (a low KD value) was E321A substituted with Ala (A) (FIG. 10D). In addition, in a direct activity ELISA-like test in which Pustulan was immobilized, mutants which had a binding activity and did not bind were confirmed, such that the same tendency was confirmed (FIG. 10E).

Figure 11:
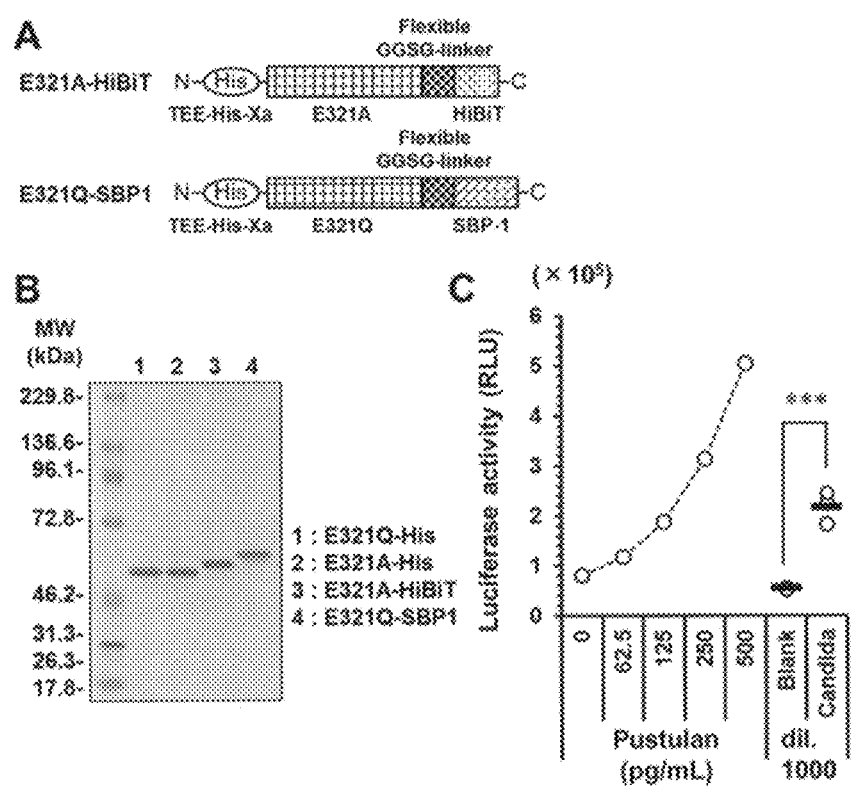
FIG. 11 is a result of high-sensitivity detection of purified β1,6-glucan and β-glucan in a fungal culture supernatant within a short period of time by a sandwich ELISA-like test using SBP-1 tag-fused β-1,6-glucanase mutant E321Q and a HiBiT tag-fused E321A immobilized on an insoluble carrier.

Example 9: Rapid Detection of β-1,6-Glucan Using Insoluble Carrier and Low Molecular Weight Tag-Fused E321Q In Example 7, it was possible to rapidly detect β-1,6-glucan using E321Q-NL by applying a known NanoLuc system (manufactured by Promega), but It was difficult to detect β-glucan in the pathogenic fungal culture supernatant with high sensitivity. Therefore, E321Q or E321A was fused and expressed with a known peptide tag to newly create E321Q-SBP1 and E321A-HiBiT. The SBP1 tag, which is a streptavidin binding tag whose amino acid sequence consists of MDEKTTGWRGGHWEGLAGELEQLRAR-LEHHPQGQREP, was prepared with reference to the literature (Wilson D S, et. al., Proc Natl Acad Sci USA. 2001 Mar. 27; 98(7):3750-5.). The HiBiT (manufactured by Promega), which is a luciferase fragment peptide tag consisting of 11 amino acids, was selected to reduce steric hindrance of NanoLuc used in Example 7, and fused to E321A having a stronger sugar chain binding ability, and expressed by *E. coli*, and then, the presence thereof was confirmed by SDS-PAGE (silver staining) (FIGS. 11A and 11B). A buffer solution having a pH more suitable for the β-glucanase mutant was newly prepared by modifying the method of Example 7. E321Q-SBP1 (50 ng) and streptavidin-labeled magnetic beads (5 μg) (manufactured by Veritas) were mixed with 50 mM Acetate buffer (pH 5.5) (AcBT) containing 1% BSA/0.05% Tween 20, E321Q-SBP1 was immobilized to a carrier, and then was added to each well of a 96-well white plate that had been previously blocked. After Pustulan, purified β-1,6-glucan, and β-glucan in a *C. albicans* culture supernatant were captured by the immobilized E321Q-SBP1 and appropriately washed, soluble E321A-HiBiT (2 ng) was bonded to β-glucan on the beads, LgBiT with high affinity to a HiBiT tag and their substrate, Furimazine (manufactured by Promega), were added thereto, and a luminescence level was measured. As a result, not only purified Pustulan but also β-glucan in the fungal culture supernatant that failed to be detected in Example 7 was successfully detected with high sensitivity within a short period of time (within 30 minutes) (FIG. 11C).

Example 10: Monitoring Blood β-1,6-Glucan

Figure 12:
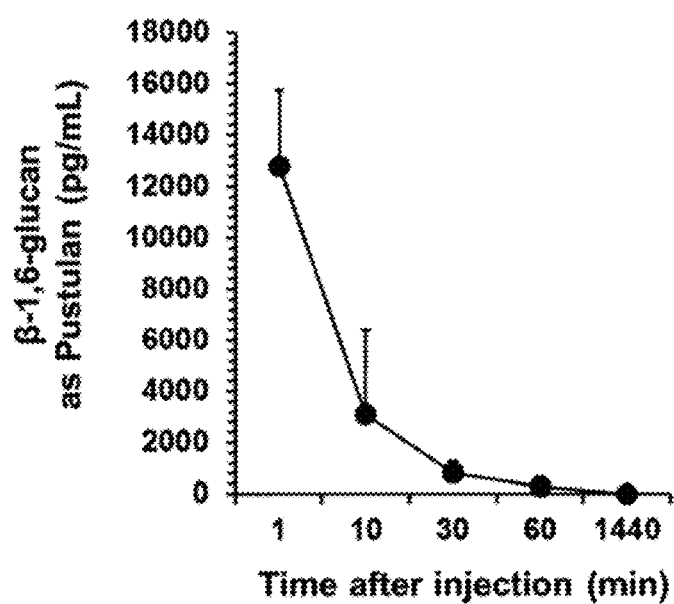
FIG. 12 is a result obtained by administering a supernatant of Candida albicans cultured for 24 hours using a serum-supplemented medium to mice via the tail vein and measuring a concentration of β-1,6-glucan in the blood depending on a time using a β-1,6-glucanase mutant.

Detection of β-1,6-glucan in the mouse blood was attempted using the same method as in Example 9. 500 uL of *C. albicans* culture supernatant prepared in the same manner as in Example 6 was administered to the tail vein of 5-week-old female ICR mice (Japan SLC) (n=3). A supernatant obtained by collecting the tail vein blood after 1 minute, 10 minutes, 30 minutes, 60 minutes and 1440 minutes (24 hours) after administration using heparinized blood collection tubes (manufactured by Wako), diluting the collected tail vein blood 10 to 20 times with AcBT, and heating the diluted tail vein blood at 80° C. for 5 minutes was used for blood concentration measurement. β-1,6-glucan derived from *C. albicans* was detectable immediately after administration until 60 minutes, but the blood concentration decreased within a relatively short period of time, such that the blood concentration was below a detection limit after 24 hours (FIG. 12). The study constructed according to the present invention can be used as not only a diagnostic aid for deep mycosis, but also a material for judging the end of therapy during using an antifungal agent.

SEQUENCE LIST

The invention claimed is:

1. A β-1,6-glucanase mutant E321X which is a mutant of β-1,6-glucanase (EC 3.2.1.75), wherein a Glu (E) residue located at a position corresponding to Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H).

2. A β-1,6-glucanase mutant E225X/E321X which is a mutant of β-1,6-glucanase (EC 3.2.1.75), wherein a Glu (E) residue located at a position corresponding to each of Glu (E)-225 and Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H).

3. A method for measuring β-1,6-glucan, comprising measuring β-1,6-glucan bonded to the β-1,6-glucanase mutant E321X according to claim 1.

4. A β-1,6-glucan measuring reagent containing the β-1,6-glucanase mutant E321X according to claim 1.

5. A β-1,6-glucan measuring reagent containing a labeled mutant E321X obtained by adding a labeling substance to the β-1,6-glucanase mutant E321X according to claim 1.

6. A β-1,6-glucan measuring kit containing a reagent (a) and a reagent (b), wherein reagent (a) is a β-1,6-glucanase mutant E321X which is a mutant of β-1,6-glucanase (EC 3.2.1.75), wherein a Glu (E) residue located at a position corresponding to Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H), or a β-1,6-glucanase mutant E225X/E321X which is a mutant of β-1,6-glucanase (EC 3.2.1.75), wherein a Glu (E) residue located at a position corresponding to each of Glu (E)-225 and Glu (E)-321 in SEQ ID NO: 1 is substituted by an amino acid residue X selected from the group consisting of Gln (Q), Gly (G), Ala (A), Leu (L), Tyr (Y), Met (M), Ser (S), Asn (N), and His (H), and reagent (b) is a labeled mutant E321X obtained by adding a labeling substance to the β-1,6-glucanase mutant E321X, or a labeled mutant E225X/E321X obtained by adding a labeling substance to the β-1,6-glucanase mutant E225X/E321X.

7. The β-1,6-glucan measuring kit according to claim 6, wherein the β-1,6-glucanase mutant E321X and/or the β-1,6-glucanase mutant E225X/E321X are immobilized to an insoluble carrier.

8. A method for measuring β-1,6-glucan, comprising measuring β-1,6-glucan bonded to the β-1,6-glucanase mutant E225X/E321X according to claim 2.

9. A β-1,6-glucan measuring reagent containing the β-1,6-glucanase mutant E225X/E321X according to claim 2.

10. A β-1,6-glucan measuring reagent containing a labeled mutant E225X/E321X obtained by adding a labeling substance to the β-1,6-glucanase mutant E225X/E321X according to claim 2.

* * * * *

SEQUENCE LISTING

<160> NUMBER OF SEQ ID NOS: 1

<210> SEQ ID NO 1

<211> LENGTH: 480
<212> TYPE: PRT
<213> ORGANISM: Neurospora crassa
<300> PUBLICATION INFORMATION:
<308> DATABASE ACCESSION NUMBER: CAF06053
<309> DATABASE ENTRY DATE: 2009-07-17
<313> RELEVANT RESIDUES IN SEQ ID NO: (1)..(480)

<400> SEQUENCE: 1

```
Met Tyr Pro Pro Ala Leu Thr Leu Leu Leu Thr Pro Gly Leu Val Ala
1               5                   10                  15

Ala Ala Ile Gln Pro Gln Ala Tyr Ala Ser Ser Ala Asp Gly Arg Tyr
            20                  25                  30

Lys Leu Ser Ser Tyr Ser Ala Pro Val Arg Gly Thr Gly Thr Pro Gly
        35                  40                  45

Ser Asn Ser Thr Trp Lys Leu Thr Ile Asp Asp Thr Pro Ser Gly Arg
    50                  55                  60

Lys Gln Thr Ile Lys Gly Phe Gly Ala Ala Val Thr Asp Ser Thr Val
65                  70                  75                  80

Ser Val Phe Asn Ala Leu Pro Ser Ala Gln Arg Thr Ala Leu Leu Asn
                85                  90                  95

Thr Leu Met Thr Thr Ala Gly Ala Asn Phe Ala Met Met Arg His Thr
            100                 105                 110

Ile Ala Ser Ser Asp Leu Ser Ala Asn Pro Ala Tyr Ser Tyr Asp Asp
        115                 120                 125

Ser Asn Gly Gln Thr Asp Leu Ser Leu Ser Asn Phe Asn Leu Gly Gly
    130                 135                 140

Arg Gly Asn Ala Met Ala Ser Leu Leu Ala Glu Met Arg Arg Leu Gln
145                 150                 155                 160

Pro Gly Leu Thr Ile Leu Gly Ser Pro Trp Ser Pro Pro Gly Trp Met
                165                 170                 175

Lys Leu Asn Arg Ala Ile Gln Gly Thr Thr Val Asn Asn Leu Asp
            180                 185                 190

His Ala Tyr Ala Ser Gln Phe Ala Gln Tyr Phe Val Lys Tyr Leu Gln
        195                 200                 205

Ala Tyr Gln Ala Lys Gly Ala Thr Ile Asp Ala Ile Thr Ile Gln Asn
    210                 215                 220

Glu Pro Leu Asn Ser Arg Ala Gln Met Pro Thr Met Tyr Ile Tyr Ala
225                 230                 235                 240

Asp Glu Ala Gly Asp Leu Ile Gln Asn Asn Ile Gly Pro Ala Leu Arg
                245                 250                 255

Asn Ala Gly Leu Asp Thr Lys Ile Trp Ala Tyr Asp His Asn Thr Asp
            260                 265                 270

Gln Pro Ser Tyr Pro Ser Thr Val Leu Ser Arg Ala Gly Gly Tyr Val
        275                 280                 285

Pro Ala Val Ala Trp His Cys Tyr Ala Ser Ser Leu Asp Trp Ser Val
    290                 295                 300

Leu Thr Thr Phe His Asn Ala His Pro Gly Val Glu Gln Tyr Met Thr
305                 310                 315                 320

Glu Cys Trp Thr Ser Ala Lys Gln Pro Thr Pro Trp Asn Trp Ala Ala
                325                 330                 335

Ser Phe Thr Met Gly Pro Leu Gln Asn Trp Ala Ser Gly Val Thr Ala
            340                 345                 350

Trp Val Leu Gly Thr Asp Thr Asn Asp Gly Pro His Leu Thr Gly Ser
        355                 360                 365
```

-continued

```
Asp Ala Cys Asp Lys Cys Thr Gly Leu Val Thr Val Asp Ala Ala Ala
    370             375             380

Gly Thr Tyr Asn Leu Arg Gly Asp Tyr Tyr Met Met Ala Gln Phe Ser
385             390             395             400

Lys Phe Met Lys Lys Gly Ala Val Val Met Ser Gly Thr Gly Ser Trp
            405             410             415

Thr Tyr Gly Asp Gly Ser Gly Leu Glu Ser Val Ala Ala Thr Asn Ala
            420             425             430

Asp Asp Gly Ser Arg Val Val Val Ile Glu Asn Lys Phe Gly Asn Glu
            435             440             445

Ile Tyr Val Thr Val Glu Ala Lys Ser Gly Glu Val Trp Ser Gly Leu
    450             455             460

Val Tyr Arg Asn Ser Val Val Thr Trp Val Leu Pro Ala Ala Gly Ala
465             470             475             480
```